US00PP21105P2

(12) United States Plant Patent
Zhao et al.

(10) Patent No.: US PP21,105 P2
(45) Date of Patent: Jun. 29, 2010

(54) ***CHRYSANTHEMUM* PLANT NAMED 'TAIHANG'S GALAXY'**

(50) Latin Name: *Chrysanthemum (X)× Opisthopappus (C)*
Varietal Denomination: Taihang's Galaxy

(76) Inventors: Huien Zhao, Department of Ornamental Horticulture, College of Landscape Architecture, Beijing Forestry University, 100083 (CN); Junyu Chen, Department of Ornamental Horticulture, College of Landscape Architecture, Beijing Forestry University, 100083 (CN); Qixiang Zhang, Department of Ornamental Horticulture, College of Landscape Architecture, Beijing Forestry University, 100083 (CN); Wenchao Liu, Department of Ornamental Horticulture, College of Landscape Architecture, Beijing Forestry University, 100083 (CN); Deyan Yang, Department of Ornamental Horticulture, College of Landscape Architecture, Beijing Forestry University, 100083 (CN); Xiao Hu, Department of Ornamental Horticulture, College of Landscape Architecture, Beijing Forestry University, 100083 (CN)

( * ) Notice: Subject to any disclaimer, the term of this patent is extended or adjusted under 35 U.S.C. 154(b) by 0 days.

(21) Appl. No.: 12/378,862

(22) Filed: Feb. 20, 2009

(51) Int. Cl.
*A01H 5/00* (2006.01)

(52) U.S. Cl. ..... Plt./284

(58) Field of Classification Search ..... Plt./263.1, Plt./284, 294
See application file for complete search history.

*Primary Examiner*—June Hwu
(74) *Attorney, Agent, or Firm*—Penny J. Aguirre

(57) ABSTRACT

A new cultivar of *Chrysanthemum,* 'Taihang's Galaxy', characterized by it's late season blooming habit with single daisy-type fragrant inflorescences with white ray florets and gold disk florets, its hybrid vigor, its prostrate to cascading growth habit after one or two years of growth, its massive floral display, and its cold hardiness to at least U.S.D.A. 5.

2 Drawing Sheets

Botanical classification *Chrysanthemum* (*X*)× *Opisthopappus* (*C*)

Variety denomination

'Taihang's Galaxy'

BACKGROUND OF THE INVENTION

The present invention relates to a new and distinct cultivar of garden *Chrysanthemum* plant, botanically known as *Chrysanthemum* (*X*)×*Opisthopappus* (*C*) 'Taihang's Galaxy' and will be referred to hereinafter by its cultivar name, 'Taihang's Galaxy'. The new cultivar is commercially known as a garden-type *Chrysanthemum.*

'Taihang's Galaxy' was derived from a controlled breeding program using *Opisthopappus taihangensis,* a native species from Northern China previously unknown to cultivation and an unnamed selection of *Chrysanthemum dichrum.* The goal of the breeding program was to develop garden type *Chrysanthemum* cultivars suitable for hanging baskets, green roofs and walls, and ecological restoration of hillsides and slopes based on their prostrate or cascading growth characteristics and drought resistance.

The new cultivar derived from a controlled cross made in 2006 in Beijing, China between an unnamed plant of *Chrysanthemum dichrum* as the male parent and an unnamed selection of *Opisthopappus taihangensis* as the female parent. 'Taihang's Galaxy' was selected by the Inventors as a single unique plant (Accession No. 20080601) from the resulting progeny in the autumn of 2007.

Asexual reproduction of the new cultivar was first accomplished by one of the Inventors using stem cuttings in the spring of 2008 in Beijing, China. The characteristics of this cultivar have been determined to be stable and are reproduced true to type in successive generations.

SUMMARY OF THE INVENTION

The following traits have been repeatedly observed and are determined to be the characteristics of the new cultivar of *Chrysanthemum.* These attributes in combination distinguish 'Taihang's Galaxy' as unique from and all other varieties of *Chrysanthemum* known to the Inventors.

1. 'Taihang's Galaxy' has a growth habit that makes it particularly suited for use in hanging baskets and for use as a perennial groundcover in sites with full sun exposure.
2. 'Taihang's Galaxy' exhibits a late-season blooming habit and exhibits single daisy-type inflorescences about 3.5 cm in diameter with white ray florets and golden disk florets.
3. 'Taihang's Galaxy' exhibits a prostrate or pendulous habit in the second and successive years of growth attaining about 25 cm in height and 30 to 50 cm in width in the first year and about 30 cm in height and 60 to 180 cm in width in the second year.
4. 'Taihang's Galaxy' exhibits extreme hybrid vigor.
5. 'Taihang's Galaxy' exhibits a massive floral display in its second and subsequent years after planting with about 1000 inflorescences produced.

6. 'Taihang's Galaxy' is a hardy shrub *Chrysanthemum* with cold hardiness at least to U.S.D.A. Zone 5.
7. 'Taihang's Galaxy' is an intergeneric hybrid.

'Taihang's Galaxy' differs from the female parent, *Opisthopappus taihangensis,* by having smaller flowers, different shaped leaves (more elongated), branches that are softer in texture and in maturing into a plant that is a little higher in height, 'Taihang's Galaxy' is similar to the male parent, *Chrysanthemum dichrum* in plant size and in having a prostrate growth habit. *Chrysanthemum dichrum* differs from 'Taihang's Galaxy' in having yellow ray florets, smaller inflorescences with shorter ray florets, and in having an earlier flowering period. 'Taihang's Galaxy' can be compared a unnamed hybrid between *Opisthopappus taihangensis* and *Dendranthema lavandulifolium,* which has similar flowers in size and color and leaves that is similar in shape. The unnamed hybrid differs in lacking the prostrate growth habit, in having a coarser branch texture, and in producing less inflorescences. There are no cultivars of *Chrysanthemum* known to the Inventors that are similar for comparison to 'Taihang's Galaxy'.

BRIEF DESCRIPTION OF THE DRAWINGS

The accompanying colored photographs illustrate the overall appearance and distinct characteristics of the new *Chrysanthemum.* The photographs were taken of plants one or two years in age as grown outside on the side of a greenhouse in Beijing, China. The photograph in FIG. 1 provides a close-up view of the inflorescences of 'Taihang's Galaxy' in early October (at the beginning of peak bloom). The photograph in FIG. 2 was taken in early October and provides of view of the plant habit and abundance of inflorescences of 'Taihang's Galaxy'. The photograph in FIG. 3 provides a comparison of single flower (capitulum) of *Opisthopappus taihangensis* (female parent) on the bottom left, 'Taihang's Galaxy' on the top left, and reciprocal hybrids between *Opisthopappus taihangensis* and *Chrysanthemum lavandulifolium* (syn. *Dendranthemum lavendulifolium*) on the top right and bottom right. The photograph in FIG. 4 provides a comparison of single leaves of *Opisthopappus taihangensis* (female parent) on the left, *Chrysanthemum dichrum* (male parent) on the right, and 'Taihang's Galaxy' in the center. The colors in the photograph may differ slightly from the color values cited in the detailed botanical description, which accurately describe the colors of the new *Chrysanthemum.*

DETAILED BOTANICAL DESCRIPTION

Figure 1:
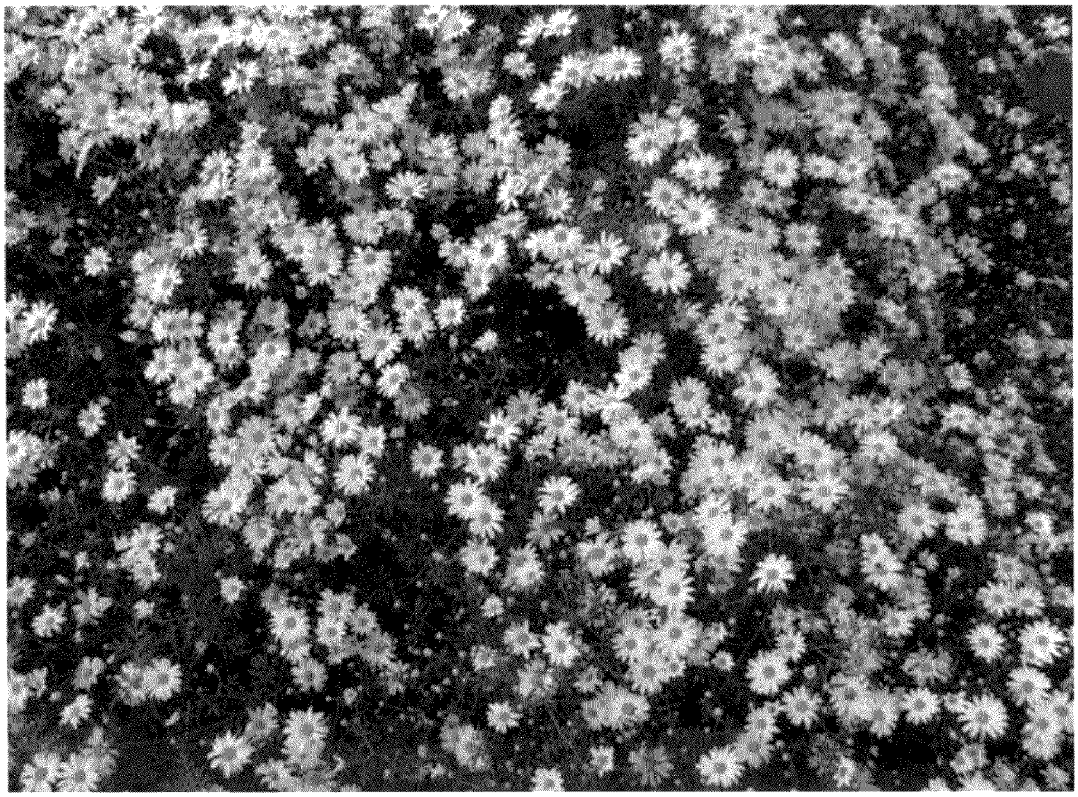
Figure 2:
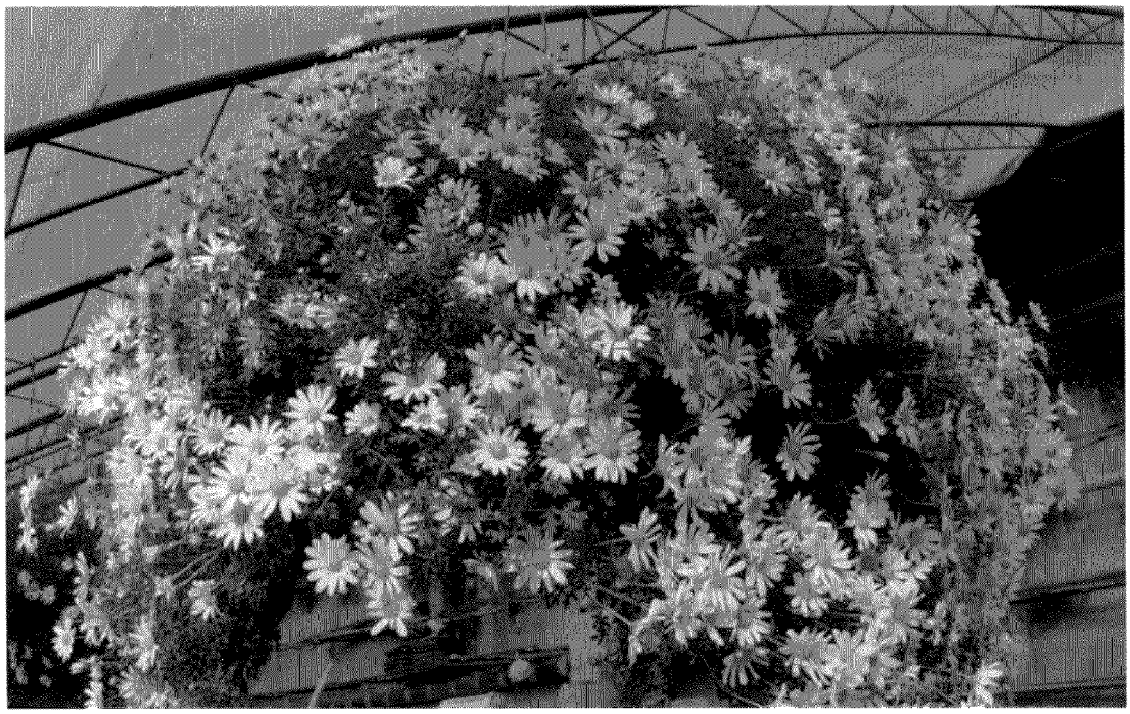
Figure 3:
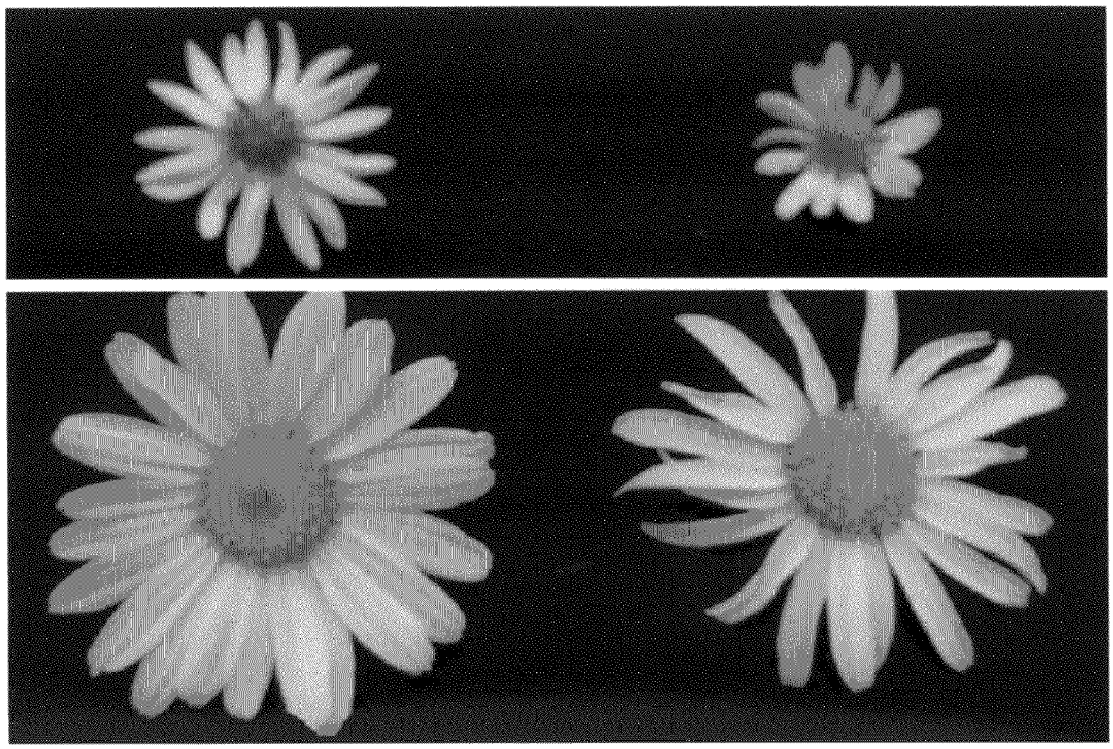
Figure 4:
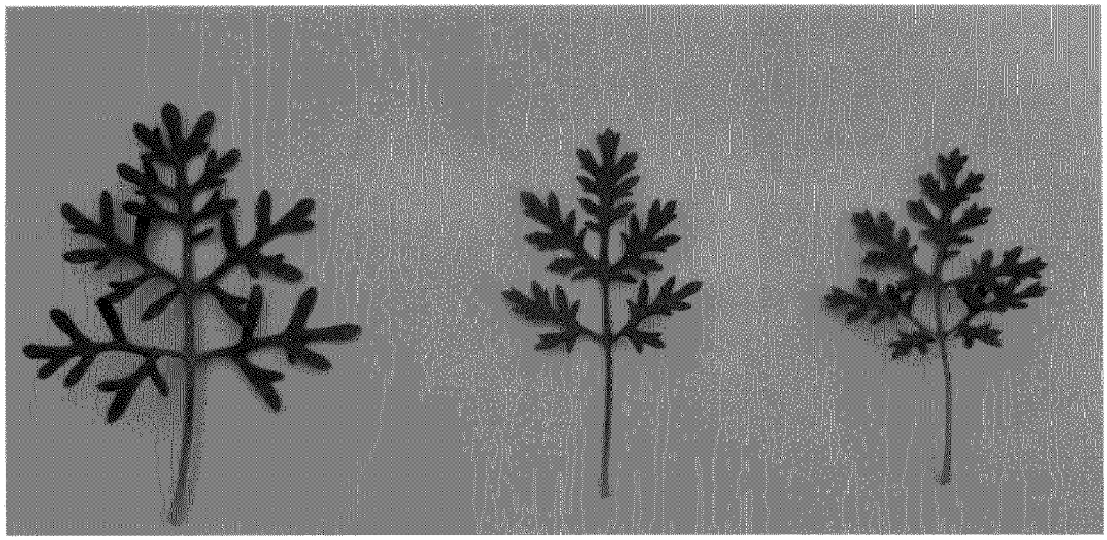

The following is a description of 2 year-old plants of the new cultivar as grown outdoors on the side of a greenhouse in Beijing, China. The detailed botanical data was taken in October 2008. The phenotype of the new cultivar may vary with variations in environmental, climatic, and cultural conditions, as it has not been tested under all possible environmental conditions. The color determination is in accordance with the 2001 RHS Colour Chart of the Royal Horticultural Society, London, England, except where general color terms of ordinary dictionary significance are used.

General Description:

*Blooming season.*—Late season after 10 weeks of short days, approximately October $5^{th}$ through October $22^{nd}$ in Beijing, China.

*Plant habit.*—Herbaceous perennial, matures to a prostrate and pendulous habit with dense branching, suitable for hanging baskets and for use as a groundcover.

*Height and spread.*—Reaches about 25 cm in height and 30 to 50 cm in width in the first year. In the second year of growth reaches 30 cm in height and 60 to 180 cm in width in the second year of growth.

*Hardiness.*—At least to U.S.D.A. Zone 5.

*Diseases resistance.*—No susceptibility or resistance to diseases common to *Chrysanthemum* has been observed.

*Root description.*—Fibrous.

Growth and Propagation:

*Propagation.*—Stem cuttings.

*Time to root initiation.*—About 2 weeks.

*Crop maintenance.*—No pinching or pruning is required to achieve a spreading to cascading habit and abundant bloom.

*Growth rate.*—Vigorous.

Stem Description:

*Stem color.*—142A first year growth, second year growth near 22A.

*Stem surface.*—Pubescent.

*Lateral branch length.*—Average of 20 to 40 cm (one year-old plant).

*Lateral branch diameter.*—Average of 4 mm (one year-old plant).

*Quantity of lateral branches.*—About 160 lateral branches per plant produced per stem if apical meristem is removed (pinched).

*Internode length.*—Variable.

Foliage Description:

*Leaf division.*—Simple.

*Leaf shape.*—Blade is ovate with narrow region extending towards base.

*Leaf base.*—Cuneate (blade), truncate (narrow base).

*Leaf apex.*—Acute to mucronate.

*Leaf margin.*—Incised (mulberry-like incisions) to average of 5 mm deep, incisions are also incised with 1 to 2 incisions 2 mm in depth.

*Internode length.*—Average of 1 cm.

*Leaf Venation.*—Upper surface 134A, lower surface 149B.

*Leaf attachment.*—Sessile.

*Leaf arrangement.*—Alternate.

*Leaf number.*—Average of 4 to 10 per lateral branch, about 1500 per plant.

*Leaf surface.*—Puberulent on upper surface, pubescent on lower surface.

*Leaf color.*—Young foliage; upper surface 134A, lower surface 149D, mature foliage; upper surface 130A, lower surface 150C.

*Leaf size (fully expanded).*—Average of 7.5 cm in length and 5.5 cm in width.

*Stipels.*—Lanceolate in shape, about 5 mm in width and 1.5 mm in length, color and surface the same as leaves.

*Leaf Fragrance.*—Fragrant if bruised.

Flower Description:

*Inflorescence type.*—Composite, single daisy-type.

*Flowering response.*—10 weeks of short days.

*Lastingness of inflorescence.*—Temperature dependent, under normal field conditions during the fall, flowers typically last about 2 weeks.

*Fragrance.*—Typical of *Opisthopappus,* very fragrant.

*Quantity of inflorescences.*—About 1000 flowers per plant (two year old field grown plant).

*Inflorescence buds.*—About 3 mm in depth and 5 mm in diameter, globose in shape, 155C in color.

*Inflorescence size.*—About 3.5 cm in diameter and 0.6 cm in diameter, diameter of disk about 0.7 cm.

*Peduncle.*—Intermediate in strength, held at various angles to the stem, texture is slightly pubescent, first peduncle is an average of 10 cm in length and fourth peduncle is an average of about 5 cm in length, color is 143B.

*Involucral bracts* (*phyllaries*).—130B in color, about 4 mm in length and 0.5 mm in width, puberulent surface.

Ray Florets (pistillate):

*Number.*—Average of 15.

*Shape.*—Oblanceolate.

*Aspect.*—Primarily horizontal.

*Size.*—Average of 15 cm in length and 0.4 cm width.

*Petal apex.*—Rounded.

*Petal base.*—Attenuate.

*Petal margins.*—Entire.

*Petal texture.*—Smooth, glabrous.

*Petal color.*—Opening and mature; upper and lower surface: whiter than 155A and fading to N155B.

Disk Florets (perfect):

*Quantity.*—Average of 60.

*Shape.*—Tubular.

*Size.*—About 5 mm in length and 1 mm in width when mature.

*Color.*—Immature; 3A, mature; 6A.

Reproductive Organs:

*Presence.*—Disk flowers are perfect, ray flowers are carpellate.

*Gynoecium.*—1 Pistil per disk and ray floret, style is 5 mm in length and 5A in color.

*Androecium.*—5 stamens per disk floret, fused into tube, anther is 2A in color, pollen is moderate in quantity and 6A in color.

*Fruit and seed.*—Very low production, none observed on the plants available for data collection.

It is claimed:

1. A new and distinct cultivar of *Chrysanthemum* plant named 'Taihang's Galaxy' as described and illustrated herein.

* * * * *